United States Patent [19]

Cullinane, Jr.

[11] 4,446,000

[45] May 1, 1984

[54] OXYGEN SENSOR AND METHOD FOR MAKING SAME

[75] Inventor: Daniel Cullinane, Jr., Tapsfield, Mass.

[73] Assignee: Lynn Products Company, Incorporated, Lynn, Mass.

[21] Appl. No.: 494,353

[22] Filed: May 13, 1983

[51] Int. Cl.³ ............................................. G01N 27/30
[52] U.S. Cl. .................................... 204/415; 204/431; 204/1 P; 204/1 R; 29/570
[58] Field of Search ............... 204/415, 431, 432, 1 P, 204/1 Y; 29/570

[56] References Cited

U.S. PATENT DOCUMENTS 3,471,394 10/1969 Sudrabin ............................. 204/435
4,187,162 2/1980 Dageforde .......................... 204/415
4,324,632 4/1982 Tantram et al. .................... 204/415

Primary Examiner—Howard S. Williams
Assistant Examiner—Terryence Chapman
Attorney, Agent, or Firm—Andrew F. Kehoe

[57] ABSTRACT

A readily adjustable oxygen sensor utilizing a wooden plug as the oxygen-limiting porous diffusion barrier.

12 Claims, 4 Drawing Figures

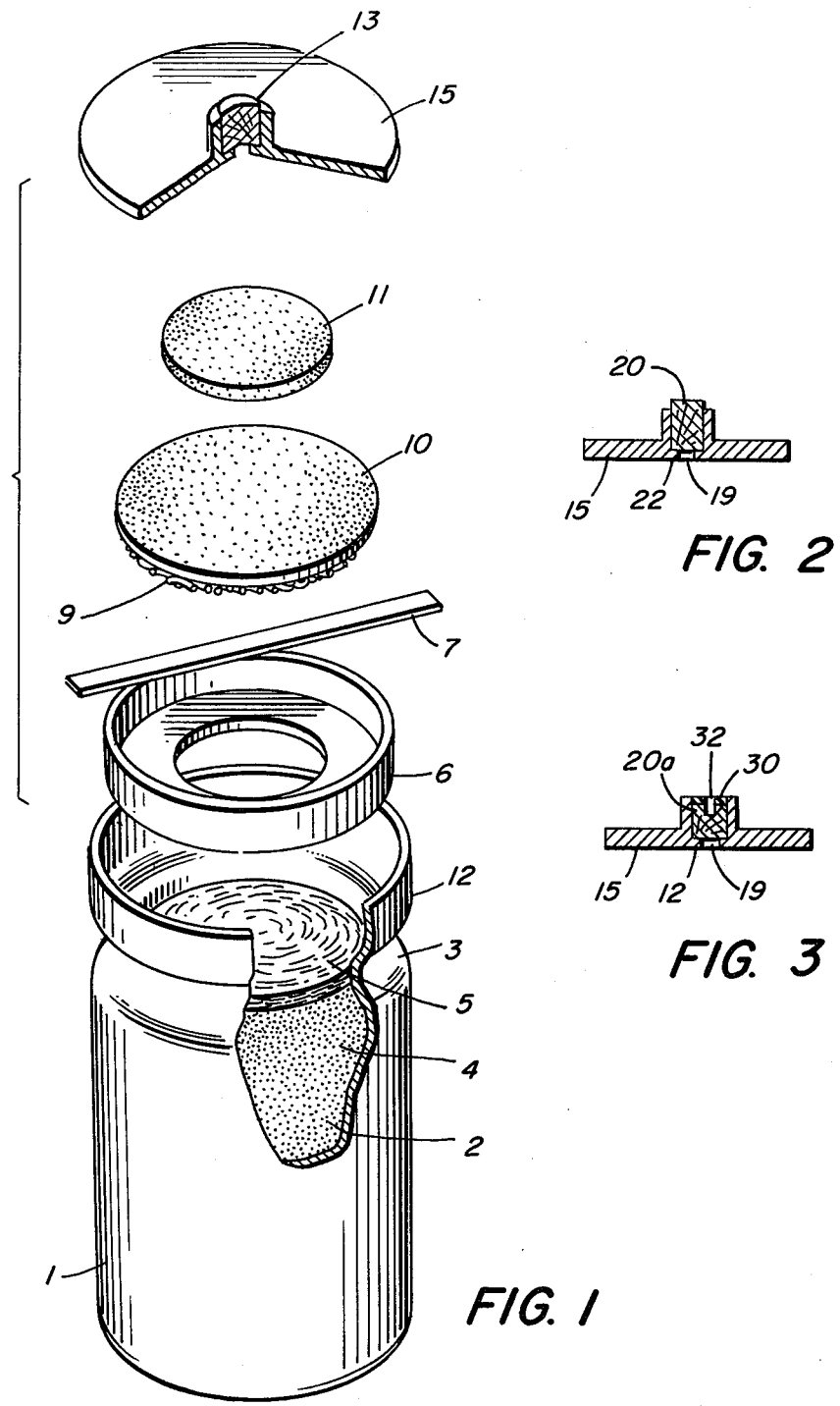

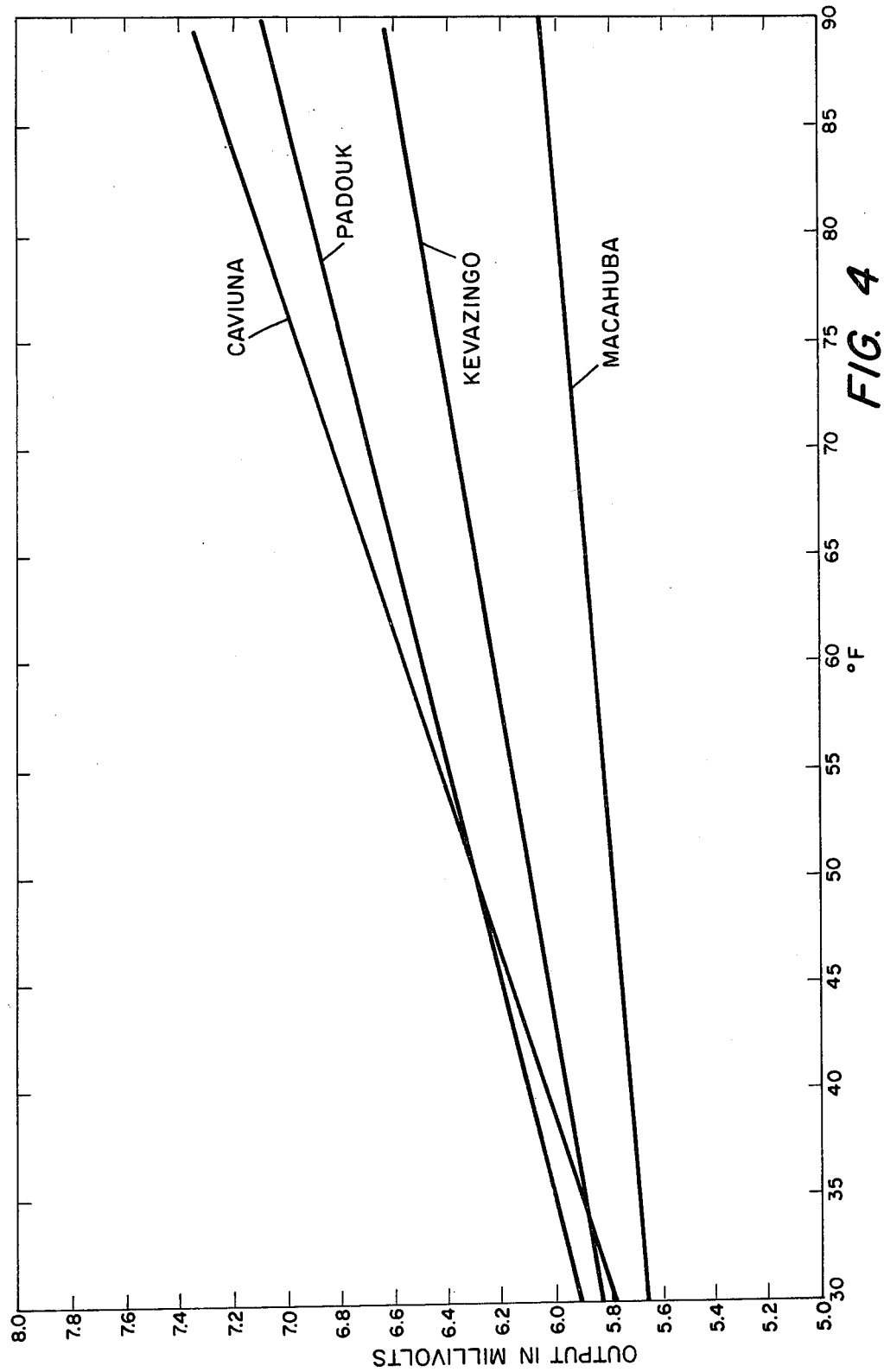

OXYGEN SENSOR AND METHOD FOR MAKING SAME

BACKGROUND OF THE INVENTION

This invention relates to electro-chemical gas sensors in which the gas or vapor to be sensed is caused to react at an electrode of an electrochemical device, thereby setting up a current through an electrolyte across the device, i.e. to a counter electrode such that the current is a function of the partial pressure of the gas to be sensed. In such cells the gas to be sensed, reaches the electrode through a diffusion path which limits the total amount of gas which actually reacts at the cell to a relatively small amount which amount, however, is a known function of, say, the concentration of gas in the atmosphere being monitored.

The prior art is replete various devices featuring diffusion-path structures ranging from thin solid membranes requiring solution of the gas in the membrane before it moves to the electrode to a Knudsen barrier type device disclosed in U.S. Pat. No. 4,324,632. U.S. Pat. No. 4,132,616 also shows a diffusion barrier which is, in large part, defined by a capillary in series with a porous body. The prior art devices are entirely suitable in performance, but it remained desirable to provide a sensor configuration that could be more readily adjusted in the field and more easily fine-tuned during manufacture.

SUMMARY OF THE INVENTION

Therefore, it is a principle object of the invention to provide a novel gas sensor which comprises a readily-adjustable diffusion barrier.

Another object is to provide a process for making a novel gas sensor, particularly an oxygen sensor.

A further object of the invention is to provide an oxygen sensor which may be conveniently adjusted after manufacture.

Other objects of the invention will be apparent to those skilled in the art upon their reading of this disclosure.

The above objects have been substantially achieved by utilizing as a diffusion-limiting barrier means a wooden plug. Preferably, the wooden plug is of hard wood. The wood may be selected from any number of trees. For example, oak, maple, and cherry woods are useful. The wood should, of course, be selected for the desired degree of diffusion. A particularly desirable wood for many general-purpose-oxygen-sensing application is Macahuba(Massaranduba).

It is possible to select different woods to give different properties. It is best that the wood be kiln dried. The wood is normally oriented so that the oxygen flow there through is parallel to the natural channels, or capillaries in the wood surface. Most such wood diffusion barriers will exhibit positive temperature coefficients. FIG. 4 shows such temperature coefficients for a number of oxygen sensors using wooden barriers as is shown in FIG. 1 and about 0.25 cm in diameter and 1.2 cm long.

The woods illustrated include Padauk (or Padouk), a tree of the genus pterocarpus, Cavinuna (or Bolivian Rosewood or Benge), a semi-tropical tree of the genus Dalbergia; Bubenga (or Kevazingo), the didelotia africana of Western Africa; and Macahuba or Massaranduba.

These woods are preferably kiln-dried and can be obtained from various commercial sources including Mr. Michael Blum of Groton, Mass.

As will be seen from FIG. 4, Macahuba wood shows the smallest temperature-coefficient while Pakouk shows the highest coefficient.

An important advantage of wood is that it can be easily fabricated, i.e. drilled with capillary-enhancing opening or filed to shorten the overall plug. The wood resists plugging under such fabricating procedures. This ready fabrication makes the resultant sensors particularly desirable for adjustment in the field.

A typical wooden diffusion barrier according to the invention would be about 0.25 cm in diameter about 1.2 cm long and will generage about 1 milliamp with a 5 ohm load when tested in air, 50 percent relative humidity and at 25° C.

ILLUSTRATIVE EMBODIMENT OF THE INVENTION

In this application and accompanying drawings there is shown and described a preferred embodiment of the invention and suggested various alternatives and modifications thereof, but it is to be understood that these are not intended to be exhaustive and that other changes and modifications can be made within the scope of the invention. These suggestions herein are selected and included for the purposes of illustration in order that others skilled in the art will more fully understand the invention and the principles thereof and will be able to modify it and embody it in a variety of forms, each as may be best suited to the condition of a particular case.

FIG. 1 is an exploded perspective of a typical sensor constructed according to the invention.

FIG. 2 is a section of diffusion-barrier structure of the invention.

FIG. 3 is another section of a diffusion-barrier structure of the invention.

FIG. 4 is a graph showing various woods and their output in millivolts of a typical sensor of the type sold by Lynn Products Company of Lynn, Massachusetts when wood diffusion barriers are used in said sensors.

The basic construction of a cell shown in FIG. 1 is similar to that illustrated in the art referred to previously and comprises a metal can 1, for example of nickel plated steel, which contains and electrically contacts a counter-electrode 2 which forms the anode when the device forms an oxygen sensor. The electrode 2 may, for example, be of a lead wool extending up to just below the level of a rill 3. The porous electrode 2 is filled with electrolyte 4, for example sodium hydroxide. A wicking separator 5 which is permeable to electrolyte but is electrically insulating is fitted on top of the electrode 2 and above this is an insulating grommet seal 6. A narrow strip of thin metal foil 7, for example silver, connects a sensing electrode 9 to the outside of a metal top cap 15 when the cell is finally closed. A waterproofing layer 10 of porous PTFE is pressed to the electrode 9 to form a unitary assembly and a porous disc 11, for example of plastic, is fitted immediately beneath the top cap 15 to ensure a good spread of diffusion of gas passing through the top cap 15. The components just described are stacked on on top of the other and the assembly is completed by folding over an upper rim 12 of the can 1 to hold all the components in position.

The top cap 15 is best shown in FIG. 2. It comprises a central bore 17 terminating in a somewhat smaller bore 19 so that the wooden plug 20 or 20a has a annular shelf 22 on which it may be snugly seated and sealed. The cap itself is then overlapped by the crimping action of rim 12. A silicone sealant, not shown, is conveniently coated over the cap 15 to aid sealing of the cap within the crimp of rim 12. The wooden plug acts as the gas diffusion limiting means.

FIG. 3 illustrates a somewhat different kind of apparatus one wherein the entire capillary of a wooden plug 20a is not required. In such a case, it is convenient to mask a portion of the plug with a resin, such as epoxy resin 30 and then drill away a portion of the epoxy resin as at 32 to expose a portion of the plug 20a. Also, of course, the drill hole can be extended a way into the plug to increase the diffusion rate and further fine tune the device.

It is also to be understood that the following claims are intended to cover all of the generic and specific features of the invention herein described and all statements of the scope of the invention which might be said to fall therebetween.

What is claimed is:

1. In an electro-chemical sensor for measuring concentrations of gas in accordance with the limiting current principle, said sensor comprising an electrolytic cell having a sensing electrode, a counter electrode and an electrolyte forming a current path between said electrodes, and a gas diffusion barrier member for restricting the rate of access of gas to said sensing electrode, the improvement wherein said restricting member is formed of wood generally aligned so the grain of the wood is parallel to the passage of said gas through said restricting member.

2. A sensor as defined in claim 1 wherein said wood is a hard wood.

3. A sensor as defined in claim 2 wherein said wood is supported on an annular surface within said sleeve effectively sealing a major portion of the diffusion capacity of that part of the wood bearing against said rib.

4. An oxygen sensor made according to the structure defined in claim 3.

5. An oxygen sensor made according to the structure defined in claim 2.

6. A sensor as defined in claim 1 wherein said wood is Macahuba (Massaranduba).

7. An oxygen sensor made according to the structure defined in claim 3.

8. A sensor as defined in claim 1 wherein said wood restricting means is largely enclosed in a close fitting sleeve but wherein up to about 0.030 inches of said wood is exposed above said sleeve.

9. An oxygen sensor constructed according to the structure defined in claim 1.

10. A sensor as defined in claim 1 wherein said wood plug comprises a partial resin seal thereover.

11. A sensor as defined in claim 10 wherein said plug has a channel drilled extending part way into said wooden plug.

12. A process for making an electro-chemical sensor of the type utilizing a limiting current principle and comprising an electrolytic cell having a sensing electrode, a counter electrode and an electrolyte forming a current path between said electrodes, and a gas diffusion barrier member for restricting the rate of access of gas to said sensing electrode, the improvement comprising the steps of utilizing a wooden restricting member, mounting said member such that it extends above the upper surface of said sensor, and adjusting the response of said sensor by machining said wooden restricting member.

* * * * *

UNITED STATES PATENT AND TRADEMARK OFFICE
CERTIFICATE OF CORRECTION

PATENT NO. : 4,446,000

DATED : May 1, 1984

INVENTOR(S) : Daniel Cullinane, Jr.

It is certified that error appears in the above-identified patent and that said Letters Patent is hereby corrected as shown below:

Column 4, line 12, "3" should read -- 6 --.

Signed and Sealed this

Seventh Day of May 1985

[SEAL]

Attest:

DONALD J. QUIGG

Attesting Officer    Acting Commissioner of Patents and Trademarks